AZALEA PLANT
Filed Nov. 25, 1974
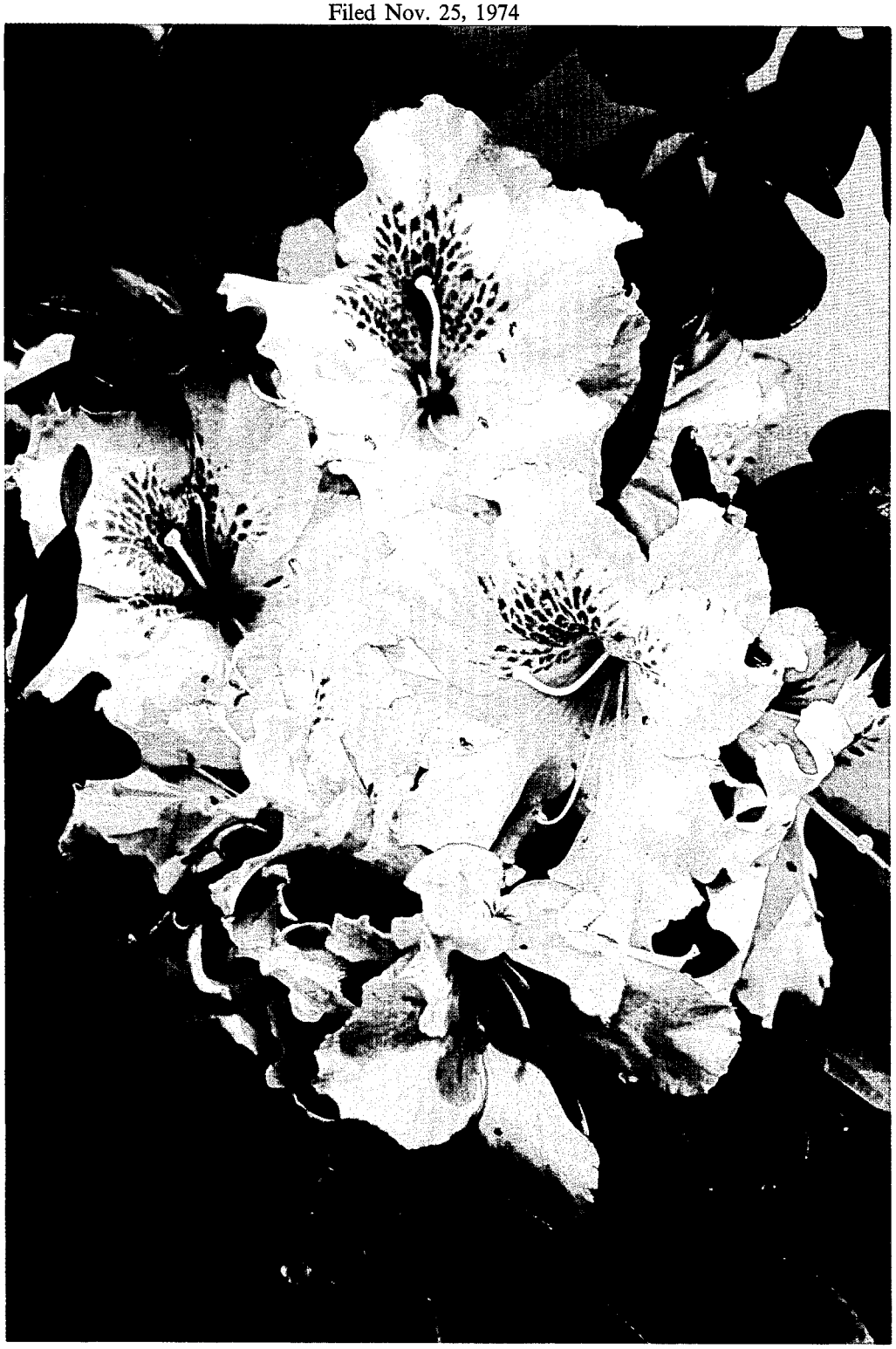

United States Patent

Plant Pat. 3,894

Patented May 25, 1976

3,894

AZALEA PLANT

James W. Hines, Jr., Corona del Mar, Calif., assignor to Hines Wholesale Nurseries, Santa Ana, Calif.

Filed Nov. 25, 1974, Ser. No. 526,619

Int. Cl. A01h *5/00*

U.S. Cl. Plt.—56 1 Claim

The present invention relates to a new and distinct variety of azalea plant. This plant was originated by me in March 1957, by crossing the azalea variety of the Southern Indica strain, Azalea "Twilight" (unpatented) with the azalea variety of the Belgian Indica strain, Azalea "Twilight"/Azalea "Wm. Van Orange" (unpatented). The seeds which were produced by this hybridization were first sown in September 1957, and the plant first bloomed in March 1958.

As a result of this breeding, I have produced a new and improved azalea variety which is endowed with the following unique combination of characteristics which are outstanding therein, and which distinguish the same from its parents, as well as from all other varieties of which I am aware.

The plant is characterized as to novelty by its ability to grow and flower in full sun or light shade in the Southern California area without tip burning of the leaves or blasting of the flowers; by its abundant and rich green foliage and compact and dense habit of growth; by the unique coloring of its flowers; and by its profuse flowering.

The new variety has been asexually reproduced by me on my cultivated property on the Irvine Ranch, near Santa Ana, Calif. Several hundred cuttings of this new and distinct variety have been made since March 1963, and it holds its distinguishing characteristics through succeeding propagations.

The drawings which accompany this petition show a typical view of the flowers and foliage of my new azalea variety. These are portrayed in color as fairly as can possibly be obtained by this method of illustration.

To facilitate identification of the important colors, I have used the color terminology of the R.H.S. Colour Chart issued by the Royal Horticultural Society of London.

Locally where grown and observed: On the Irvine Ranch, approximately 5 miles south of Santa Ana, Calif.

Parentage: Seedling resulting from planned propagation.

Seed parent.—Azalea "Twilight" an unpatented variety of the Southern Indica strain.

Pollen parent.—Azalea "Twilight"/Azalea "Wm. Van Orange," an unpatented variety of the Belgian Indica strain.

*The plant*

Growth: The plant is of very vigorous growth habit, with dense branching starting just above ground level. Flowering is prolific, with first blooms in late November, and heaviest bloom from late February into March. The plant is suitable for forcing. This plant has a stronger growth habit than the Belgian Indica variety, with plants in the nursery growing to a height of three feet.

Branches:

New growth is in the Greyed-Orange Group, Plates 174A to 174B, gradually changing color towards the tip to the Yellow-Green Group, Plates 153A to 153B.

Older branches are in the Greyed-Orange Group, Plates 166A to 166B.

All branches are hirsute.

Foliage: The leaves are of good substance, semi-glossy and abundant.

Shape: Elliptic with an acute tip. Leaf margins are entire and slightly hairy.

Color:

New leaves—Upper surface is in the Yellow-Green Group, Plates 144A to 144B. Underside is in the Yellow-Green Group, Plates 146B to 146C.

Mature leaves—Upper surface is in the Yellow-Green Group, Plates 146A to 146B. Underside is in the Yellow-Green Group, Plates 146B to 146C.

Size:

New leaves range from ⅞ to 1¼ inches in width, and 2⅜ to 2½ inches in length.

Mature leaves range from ⅞ to 1¼ inches in width, and 2⅜ to 2½ inches in length.

Veins: Prominent and lighter in color than leaf, running from the petiole to the tip, and having pinnate veins extending therefrom.

*The flower*

The plant first flowers in late November, with heaviest bloom in late February, extending to mid-March, with occasional blooming thereafter. The flowers are borne 2 to 7 to a stem (mostly 5), regularly clustered, with flowers appearing at both the tips of the branches, and also to mid-branch, creating a very floriferous effect.

Form: Flowers are ruffled, hose-in-hose.

Petals: 5 upper petals and 5 lower petals, and at maturity, blossoms range in size from 2¾ inches in width, to a depth of 1¾ to 1⅞ inches.

Color: The color of the flowers are entirely in the Red Group, the base of the lower petals ranging from 42B to 42D, the mid-areas of the lower petals and the bases and mid-areas of the upper petals ranging from Plates 55B and 55C to Plates 56C and 56D, and the apices of both the lower and upper petals ranging from 56C to 56D. The standard and upper wing corolla lobes have blotches ranging from Plates 46A to 46B.

Buds: Long, tapered, and in the Red Group, shading from Plates 52B to 52C.

Reproductive organs: 6 stamens with the color in the White Group, Plates 155A to 155B. They range from 1 to 1⅜ inches in length.

Pollen—Greyed-Orange Group, Plates 170G to 170D.

I claim:

1. A new and distinct variety of azalea plant which is a hybrid of the Belgian Indica strain and the Southern Indica strain, and characterized in particular to novelty by its ability to grow and flower in full sun or light shade in the Southern California area without tip burning of the leaves or blasting of the flowers; by its abundant and rich green foliage and compact and dense habit of growth; by the unique coloring of its flowers; and by its profuse flowering; and by its greater salts tolerance, making it less subject to root diseases common to other varieties grown in the same general area of the Irvine Ranch in Southern California.

No references cited.

ROBERT E. BAGWILL, Primary Examiner